United States Patent [19]

Huntley et al.

[11] Patent Number: 5,541,056

[45] Date of Patent: Jul. 30, 1996

[54] METHOD OF CONTROL OF MICROORGANISM GROWTH PROCESS

[75] Inventors: Mark E. Huntley, Honolulu, Hi.; Pearn P. Niiler, La Jolla, Calif.; Donald Redalje, Pass Christian, Miss.

[73] Assignee: Aquasearch, Inc., La Jolla, Calif.

[21] Appl. No.: 279,740

[22] Filed: Jul. 22, 1994

Related U.S. Application Data

[63] Continuation-in-part of Ser. No. 23,172, Feb. 25, 1993, abandoned, which is a continuation of Ser. No. 729,707, Jul. 15, 1991, abandoned, which is a division of Ser. No. 663,669, Mar. 1, 1991, abandoned, which is a continuation-in-part of Ser. No. 419,522, Oct. 10, 1982, abandoned.

[51] Int. Cl.$^6$ .............................. C12Q 3/00; C12M 1/36
[52] U.S. Cl. .................. 435/3; 435/240.46; 435/257.1; 435/257.3; 435/286.5; 435/292.1; 47/1.4
[58] Field of Search .......................... 435/3, 41, 240.1, 435/240.4, 240.46, 240.47, 257.1, 257.3, 257.6, 284, 286, 289, 316, 286.1, 286.5, 289.1, 292.1, 293.1, 298.1; 47/1.4

[56] References Cited

U.S. PATENT DOCUMENTS

| | | | |
|---|---|---|---|
| 2,732,663 | 1/1956 | Dewey, II | 47/58 |
| 3,769,176 | 10/1973 | Hise et al. | 195/142 |
| 3,955,317 | 5/1976 | Gudin | 47/1.2 |
| 3,959,923 | 6/1976 | Selke | 47/1.4 |
| 4,044,500 | 8/1977 | Hitzman | 47/1.4 |
| 4,169,050 | 9/1979 | Serfling et al. | 210/12 |
| 4,209,943 | 6/1980 | Moeller et al. | 47/1.4 |
| 4,253,271 | 3/1981 | Raymond | 47/1.4 |
| 4,724,214 | 2/1988 | Mori | 435/290 |
| 4,868,123 | 9/1989 | Berson et al. | 435/290 |
| 4,952,511 | 8/1990 | Radmer | 435/314 |

FOREIGN PATENT DOCUMENTS

| | | |
|---|---|---|
| 0239272 | 9/1987 | European Pat. Off. . |
| 2118572 | 11/1983 | United Kingdom . |
| 2205581 | 12/1988 | United Kingdom . |
| 9105849 | 5/1991 | WIPO . |

OTHER PUBLICATIONS

O'Brien et al., *Applied Fluid Mechanics*, 105–110 (1st edn.: 1937).
Goldman, *Water Res.*, 13:1–19 (1979).
Anon., *Australian J. Biotech.* 1(1) (Jun., 1987), three unnumbered pages.
Emdadi et al., *Marine Biol.*, 308(III):519–525 (1989).
Thomas et al., *J. Appl. Phycol.*, 2:71–77 (1990).

*Primary Examiner*—William H. Beisner
*Attorney, Agent, or Firm*—Brown, Martin, Haller & McClain

[57] ABSTRACT

A control method for operating aqueous microorganism growth processes is disclosed which can maintain viable growth conditions for many types of microorganisms which have heretofore not been easily reproduced in commercially valuable quantities. The primary control parameters are the degree of turbulence in the aqueous growth medium and the scale of the apparatus relative to the scale of the turbulent eddies in vessels which are partially filled with the aqueous medium directly affect conditions which are required for optimum growth: light exposure, nutrient supply, sedimentation rate, bulk temperature, gas exchange rate and cell integrity. These control elements can be cast in terms of the Reynolds number ($N_{Re}$) and controlled dimensions of the apparatus ($L_K$) in relationship to the scales of turbulent eddies to define the dissipation $\lambda_K$ as $L_K/L$. Alternatively, these can be recognized to show that the delivery of nutrients to the microorganism mass is dependent upon the dissipation rate $\epsilon$ in the fluid, which allows a definition of $L_k$ to be quantified. The broadest ranges generally useful in this invention are $N_{Re}=2000$ to $10^6$, preferably 4000 to 250,000; apparatus scale relative to eddy scale is such that the level of fluid in the reaction chamber relative to eddy scale is 10–1:1 preferably 10–1.2:1; and turbulent energy dissipation rate $\epsilon$ between $10^{-3}$ and 10 W/kg. The invention is particularly useful in controlling growth processes in which the microorganisms are unicellular algae, phytoplankton, issues of vascular plants, tissues of macroalgae, and the like.

16 Claims, 1 Drawing Sheet

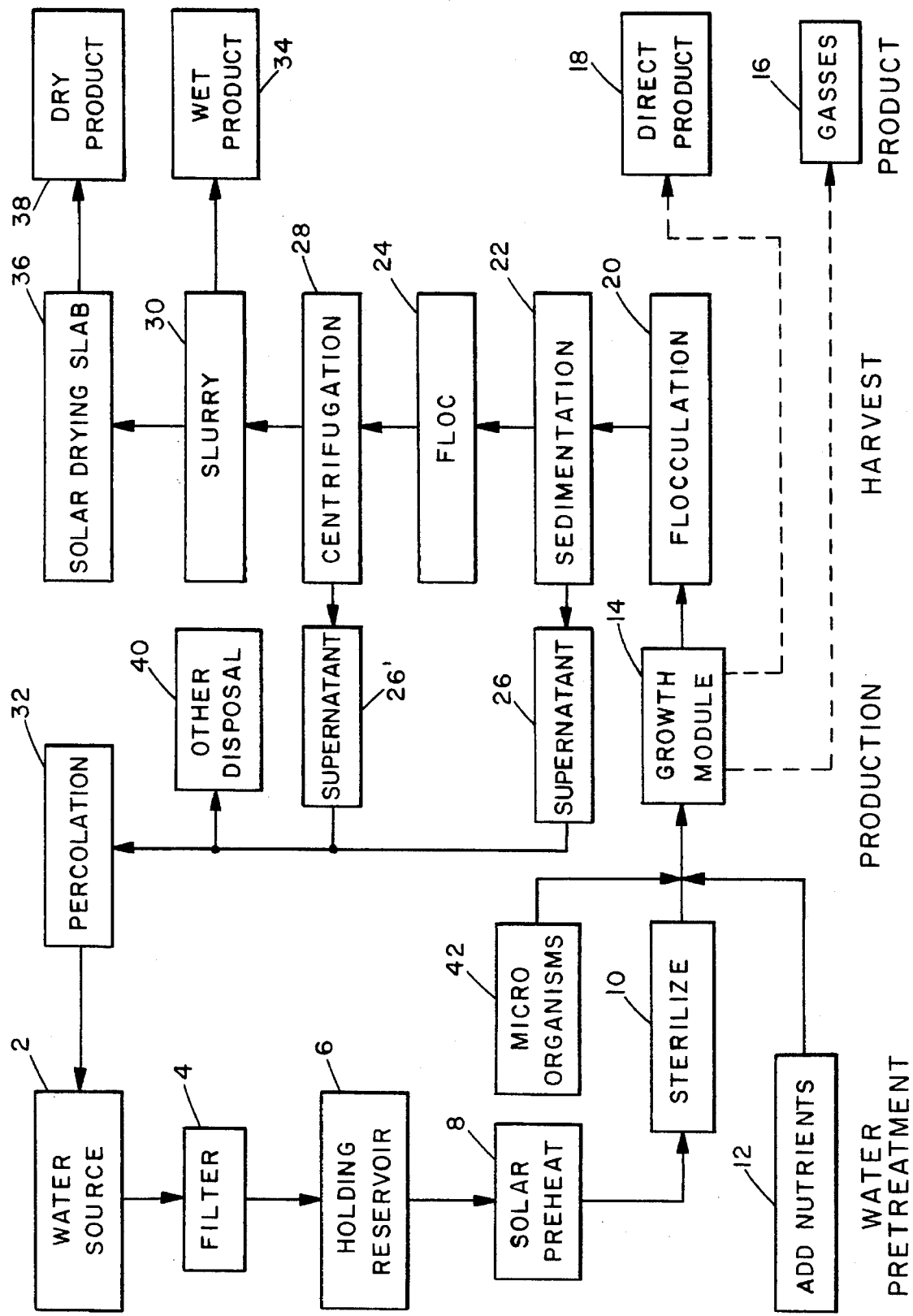

METHOD OF CONTROL OF MICROORGANISM GROWTH PROCESS

CROSS-REFERENCES TO OTHER APPLICATIONS

This application is a continuation-in-part of application Ser. No. 08/023,172, filed Feb. 25, 1993, now abandoned; which in turn is a continuation of application Ser. No. 07/729,707, filed Jul. 15, 1991, and now abandoned; which in turn is a division of application Ser. No. 07/663,669, filed Mar. 1, 1991, and now abandoned; which in turn is a continuation-in-part of application Ser. No. 07/419,522, filed Oct. 10, 1989, and now abandoned.

BACKGROUND OF THE INVENTION

1. Field of the Invention

The invention herein relates to the extraction of natural products from microorganisms, especially algae. More particularly it relates to control of large size aqueous photosynthetic bioreactor systems to obtain such products from many microbial strains which have heretofore only been cultured in laboratory environments in small containers.

2. Description of the Prior Art

In view of environmental constraints, economics, and various other factors, numerous products which are currently produced by chemical synthesis from petroleum- or coal-derived raw materials are coming into disfavor or are facing restrictions or outright bans from the marketplace. For instance, many aniline-based dyes are or will soon be phased out by government regulation in Europe, and similar restrictions or bans are likely to arise soon in other areas of the world, including the United States. Consequently there is a major research and development effort going on worldwide to find natural sources for these synthetic materials.

In the case of certain types of dyes, it has been known that dyes of substantially equivalent color and other physical properties can be obtained from certain species of microorganisms, in particular certain unicellular algae and phytoplankton. Upon exposure to light, the algae produce these dyes or dye precursors (hereinafter collectively referred to as "dyes") by photosynthesis. If such microorganisms could be cultivated on a mass production basis, a valuable and economic natural source for the dyes would be available.

The obvious utility of mass production of photosynthetic microorganisms resides in the process of photosynthesis itself. Given the appropriate supply of light, water, and carbon dioxide ($CO_2$), photosynthetic microorganisms can utilize sources of essential nutrients such as nitrogen (N) and phosphorous (P) to convert solar energy into chemical energy. Thus, the process of growing or culturing photosynthetic microorganisms involves the introduction of nutritionally complete medium to a contained volume of culture, maintenance of optimal growth conditions in that volume, and subsequent harvest or removal of the microbial cells from the spent medium. All culture programs must devise methods to accomplish each of these phases of the production process efficiently.

Of these requirements the most difficult to achieve is usually the step of maintaining optimum growth. Many of the microorganisms from which dyes are derived are very sensitive, by an order of magnitude, to small changes in their growth environment. It is common for a researcher to develop a protocol for maintaining microbial growth in the laboratory in a small volume in a laboratory container, only to have the system fail dramatically in large size volume required for economic field production, where control of system parameters is much more difficult and more variables can be encountered.

One photosynthetic growth mechanism, known as the "flashing light effect"; i.e., the ability of some photosynthetic cells to effectively use energy from an intermittent light source [see, e.g. Emerson, et al., *J. Gen Physiol.*, 15(4):391–420 (1932)], has not been effectively utilized in a mass culture system, because it depends on the turbulent flow regime in the growth media that exposes cells intermittently to a light source. Too much or too little exposure results in decreased production of microorganisms. To date, no method or apparatus has been developed which would maximize the flashing light effect by use of controlled turbulent flow regime such that this effect could be utilized in a mass culture system, thus enhancing the efficiency and productivity of that system. This need has been addressed by the present invention.

While fluid flow has been studied with respect to microalgal systems previously, the work reported taught that excessive shear in the fluid on the scale of the microorganism must be avoided in order to prevent destruction of the microbial mass. For instance, Thomas et al., *J. App. Phycology*, 2:71–77 (1990) reported that in small gap rotating cylinders at Reynolds Numbers above 116 (and up to 3500) cell growth rate became negative, i.e., that the microbial mass was dying, not growing. Thus, the dimensions or mechanical configuration of the apparatus must also be controlled in order to alleviate the deleterious effects of turbulence on cell integrity.

The concept of culturing microorganisms in open or closed systems and harvesting a product from the microorganisms is not new. There are numerous systems used throughout the world in which algae or phytoplankton are grown and harvested, either for direct usage (as for animal food) or for indirect usage (as sources of chemicals such as carotenes). However, almost all such systems operate on only a very few species of microorganisms; i.e., those which have been found to be tolerant to the widest range of growth conditions and which produce relatively simple products. This in turn has limited the industry to production of a very small number of products compared with what has been extracted in laboratory scale, experimental cultures. Efforts that have been made to culture microorganisms for production of more complex materials have been failures because laboratory cultures have not been made to survive or grow economically in large scale volumes. Furthermore, simple microorganisms which will tolerate the fairly crudely controlled processes of the past (either open or closed systems) have not been capable of yielding such desirable chemicals, either directly or indirectly, in economical quantities. More "exotic" microorganisms from which such chemicals could be produced have not proved amenable to culture in the current systems, since such systems cannot be controlled in a sufficiently precise manner to maintain adequate health and growth of the exotic microorganisms which may have been grown on a small scale in a laboratory. Laboratory scale apparatuses generally do not contain turbulent flows, while commercial production scale systems do. Heretofore, the necessity of control of turbulence has not been recognized as a crucial factor in mass culture apparatus.

Numerous factors are critical in aquaculture of useful but condition-sensitive microorganisms. Consequently, a system in which precise control of these operating conditions is accomplished will permit not only large scale culturing of many microorganisms which cannot now be grown by existing commercial technology but also the mass production of many materials which are not currently available on an economic basis in the marketplace.

SUMMARY OF THE INVENTION

The present invention is a control method for operating aqueous microorganism growth processes so as to maintain optimum and thus commercially viable growth conditions for a large number of microorganisms which have heretofore not been reproduced in commercially valuable quantities. We have discovered that such processes can be precisely and continuously controlled and can sustain the commercially viable growth of a much wider variety of microorganism types than has been possible with prior art processes and control methods. The primary control parameters in this invention are the degree of turbulence in the aqueous growth medium and the scale of the apparatus relative to the scale of the turbulent eddies. Control of the level of turbulence and the size/configuration of vessels which are either closed to the atmosphere, or in which communication with the atmosphere is restricted or controlled, and which are partially filled with the aqueous medium, directly affects the control of all the conditions which are required for optimum and thus commercially viable growth: light exposure, nutrient supply, sedimentation rate, bulk temperature, gas exchange rate and cell integrity. Thus, we have been able to successfully produce large scale quantities of condition-sensitive photosynthetic microorganisms on a sustained basis by utilizing aqueous medium turbulence and apparatus configuration relative to turbulence as the primary control parameters for optimum growth. Failure to control turbulence levels or apparatus scale leads to failure of system operations or to less than optimum growth and commercial viability (as demonstrated in Thomas, supra.).

Therefore, the invention in its broadest form is a method for the control of an aqueous microorganism growth process which comprises distributing a photosynthetic microbial biomass in an aqueous medium within a reaction chamber, the reaction chamber being transparent to visible light, and the aqueous medium containing the suspension of microbial biomass occupying less than the total volume of the chamber; maintaining the biomass within the reaction chamber for a period of time during which microorganisms comprising the biomass reproduce and increase in number; providing nutrients to and removing evolved gases from the biomass during the period of time to support the reproduction; flowing quantities of the aqueous medium through the reaction chamber throughout the time period; subjecting the reaction chamber to a source of visible light for at least a portion of the period of time with the visible light passing into the reaction chamber and being used by the microorganisms to enable photosynthesis; maintaining a turbulent flow regime with turbulent eddies predominantly throughout the aqueous medium within the reaction chamber for the period of time; maintaining a predetermined range of ratios between the scale of the chamber and the scale of the eddies for the period of time; such that in the turbulent flow regime effective reaction conditions are maintained for the reproduction of the microorganisms until the time period has been sufficient to produce a desired increase in number of the microorganisms.

In the present process of control, turbulence itself is characterized by two parameters: its time scale (t) and the space scale, L, of its predominant eddies (the scale in which viscous processes become important). The time scale of the turbulent eddies controls the time a microorganism spends in the light intensive zone of the apparatus, and thus its control is critical. The combination of L and t, as (L/t), defines the velocity scale of turbulence, q, and q controls the vertical rate of transport of microorganisms. q must be larger than the settling velocity of the microorganisms in order to keep them in suspension. Nutrient delivery to the cells is controlled by choosing optimum lengths ($L_K$) of apparatus so as to not overstress their cell walls. Removal of oxygen, which is deleterious to microorganisms, is accomplished by allowing turbulence to access significant areas of free surface in the partially filled container.

These control elements can be cast, first, in terms of the Reynolds number ($N_{Re}$). Secondly, controlled dimensions of the apparatus ($L_K$) must be specified in relationship to the scales of turbulent eddies, expressed as $\lambda_K=L_K/L$. Alternately, the second criteria can be recognized as a specification of the dissipation rate of mechanical energy in the fluid, $\epsilon$, which for a given Reynold's number allows L to be quantified for delivery of nutrients to the cell. In the present process, control of turbulence is maintained within a range of Reynolds Numbers ($N_{Re}$) and level of fluid free surface is controlled so as to exert control over the degree of light intensity, nutrient delivery, sedimentation rate and gas exchange to which the microorganisms can be exposed to obtain the optimum yield. The broadest ranges generally useful in this invention are $N_{Re}$=2000 to $10^6$, preferably 4000 to $10^6$, more preferably 4000 to 250,000, and yet more preferably 5000 to 50,000, and the level of fluid in the flowing-fluid reaction chamber relative to eddy scale, $\lambda_K$, is in the range of 10–1:1, and preferably in the range of 10–1.2:1.

The invention is particularly useful in controlling growth processes in which the microorganisms are unicellular algae, phytoplankton, tissues of vascular plants, tissues of macroalgae, and the like. Typical examples of specific genera and species whose growth on a commercially viable basis can be controlled by turbulence control include Dinophyceae, Bacillariophyceae, *Lyngbya lagerheimii* (Cyanophyceae), *Spirulina platensis* (Cyanophyceae), *Haematococcus pluvialis* (Chlorophyceae), *Chlorella sorokiniensis* (Chlorophyceae), and plant cell tissue cultures. Particularly preferred for growth by means of the claimed invention are *Haematococcus pluvialis, Spirulina platensis, Lyngbya lagerheimii*, and *Chlorella sorokiniensis.*

BRIEF DESCRIPTION OF THE DRAWING

The single FIGURE of the drawings is a flow diagram illustrating an exemplary algae production process utilizing the control method of the present invention. The control method is utilized in the design and operation of the "growth module" segment of the process.

DETAILED DESCRIPTION AND PREFERRED EMBODIMENTS

There are currently two types of aqueous systems for the growth of microorganisms, such as algae and phytoplankton. In first type, the operator produces and harvests common types of microorganisms for animal and human food consumption and for extraction of chemicals such as beta-carotene. These systems may be closed, but often are open, and use as their raw materials microorganisms which have relatively low sensitivity to reaction conditions. Simple exposure to sunlight, access to common nutrients which are coarsely dispersed in the aqueous medium, and minimal control of operating parameters such as temperature, mixing, gas exchange and the like characterize these systems. Process control often consists of little more than deciding when to stop and start the medium circulation devices and how often to inject nutrients into the medium. Such systems work quite well for production of only several species of microorganisms, and they are found throughout the world, particularly in hot and sunny climates.

However, such conventional systems have not been found capable of effectively producing a wide variety of microorganisms which are much more sensitive to the conditions of their growth environment. No algae grown in typical fermentation devices have shown commercial success to date. For example, lutein production from the alga Neospongiococcum was attempted in commercial scale fermenters (U.S. Pat. No. 3,257,210) as a source of chicken feed, but was too costly. Lutein production from Chlorella was also attempted, but was not economically feasible (U.S. Pat. No. 3,280,502). The present system, by contrast, provides light and turbulence control not provided in standard fermentation devices. Production of such microorganisms on an economic scale is highly desirable, since many such microorganisms produce, either directly or after subsequent processing, important chemicals. Unfortunately, sufficiently close and precise control of the growth environment parameters has heretofore only been possible in laboratory or equivalent small scale processes. When developers have attempted to scale up such processes, the results have usually been either an inability to duplicate the growth rates of the laboratory or short-term growth followed by mass death of the microorganism population.

There are a number of operating conditions which we have found to be important parameters to produce significant, economic and sustainable growth of "condition-sensitive" microorganisms. These include received light, type and amount of available nutrients, sedimentation rate of microorganisms, uniformity of fluid temperature of the growth medium, ability of the medium to provide for adequate gas exchange, $CO_2$ delivery or acidity (pH), and turbulence of the aqueous medium during the microorganism growth cycle. An important element in this process is the recognition that to a large extent these operating conditions in scaled up, commercially viable growth modules are controlled by turbulence levels such that control of turbulence within a partially filled physical growth chamber/reaction vessel provides operative control over these parameters. This unique control has not been present or recognized in the prior art's small scale laboratory systems, nor would it be expected from such systems.

It has long been known that the relationship of microbial growth rate to light level is a complex function, and that each type of microorganism there is a point at which increasing light level begins to have a detrimental rather than beneficial effect on growth; see Ryther, *Limnology and Oceanography*, 1:61–70 (1956) and Parsons et al., *Biological and Oceanographic Processes* (3rd Edn: 1984). Thus to obtain satisfactory algae yield the operator of a growth system must maintain the light intensity at or near the peak of the curve for the specific algae in the system. The prior art has not taught any method for accomplishing this for condition-sensitive microorganisms on an economical large-scale continuous basis.

To produce the "flashing light effect" requires an environmental regime wherein the ratio of light:no light is approximately 10:1; Laws et al., *Biotech. Bioeng*, 15:2319–2335 (1983). It is believed that this is because the photosystem becomes saturated with photons after a relatively short exposure to light, and cannot use the additional photons.

A critical feature of the present invention is that the light exposure process for the microorganisms is primarily controlled by precise control of the degree of turbulence in the aqueous medium and control of the scale of the apparatus to the scale of the turbulent eddies. Aqueous media which contain a commercially viable diversity of cells are relatively opaque due to cell density and the light penetration is often limited to a few centimeters. In this context, the level of turbulence must be maintained such that the time the microorganism spends near the light exposed surfaces of the apparatus is larger than it spends in the opaque media. This is accomplished in this invention by recycling the microorganisms near the free surface of the flowing media in the partially filled growth module, and the degree of turbulence controls the recycling. Control of the level of turbulence in the medium also directly affects gas exchange rates. Even levels of bulk temperature and availability of nutrients to the cells must be maintained. Oxygen must be removed continually; this is accomplished via recycling of the turbulent eddies coming in contact with the free surface of the partially filled growth module. Important also is the sedimentation rate during the growth process. If cells are allowed to settle on the bottom or the walls of the growth module, light penetration is inhibited and the immobile cells become detritus which harbor hostile bacteria and produce unwanted effects. Thus, as noted, in properly designed apparatus we have been able to successfully produce large scale quantities of condition-sensitive microorganisms on a sustained basis by utilizing aqueous medium turbulence as the operative control parameter. Essential to this control method is the existence of a free fluid surface across which light penetrates and across which oxygen is exchanged with the fluid.

Reynolds Number Control:

It is known that there are two principal regimes in flowing fluids, a laminar flow regime which is characterized by streamlines which remain distinct from one another over the given length of the fluid flow, and a turbulent flow regime which is characterized by an overall zone of flow instability in which eddies are generated which produce a disruption of the streamlines' flow pattern. In systems where there is an overall flow translation, e.g., a bulk fluid flow from one end of a conduit to the other, the turbulent flow regime is superimposed on the primary bulk translational flow, so that the result is a highly mixed flow stream with the mixed fluid moving along the prescribed flow path.

The transition from laminar flow to turbulent flow in a fluid body and the degree of turbulence in that body depends on the rate of movement of the fluid, the parameters of the flow conduit, and the viscosity of the fluid. Turbulence (and laminar flow) are most commonly defined numerically by a dimensionless quantity called the Reynolds Number ($N_{Re}$) which is of the form ($L_K V/v$), where $L_K$ is (as defined above) a characteristic linear dimension of the conduit, V=average flow speed of the bulk fluid flow, and v=fluid kinematic viscosity. The "critical Reynolds Number" [$N_{Re}$(crit)] is the $N_{Re}$ value of the transition from laminar flow to turbulent flow in the fluid of interest. For circular conduits $N_{Re}$(crit) is 2000–4000, depending upon the wall roughness of the conduit; i.e., transition from laminar flow beings at $N_{Re} \leq 2000$ and a turbulent flow regime is well established once $N_{Re}=4000$. There is no specific upper limit to values of $N_{Re}$, with published tables commonly showing highly turbulent regimes with $N_{Re}$ up to $10^8$, although for flow in conduits of common materials fluids tend to reach a maximum turbulence regime at $N_{Re}$ values of about $10^6$ and thereafter higher values of $N_{Re}$ generally do not signify substantially more turbulence in the fluid. Derivation and explanation of Reynolds Number are found in many fluid dynamics handbooks and textbooks; see, e.g., Chilton (ed.), *Chemical Engineers' Handbook*, pp. 5–4 and 5–20 to 5–26 (5th edn.: 1973); Condon et al. (eds.), *Handbook of Physics*, Part 3, Ch. 2 (1958); Eshbach (ed.), *Handbook of Engineering Fundamentals*, Sect. 6, Parts 2, 6 and 9 (2nd edn.: 1952); Weast (ed.), *Handbook of Chemistry and Physics*, p. F-330 (65th ed.: 1984); and O'Brien et al., *Applied Fluid Mechanics*, pp. 105–110 (1st edn.: 1937).

Note that when the turbulent flow regime is mentioned herein, and especially when it is discussed as being essentially throughout the aqueous medium in the reaction vessel, it will be understood that some small degree of laminar flow regime will necessarily also be present, normally in the boundary layer immediately adjacent to the vessel walls. It is known that in any flowing fluid conduit, a viscous Prandtl boundary layer will form at the surface of the vessel walls, with the layer including a laminar flow region at the wall transistioning to a turbulent flow region in the body of the fluid. The degree of turbulence in the body of the fluid will affect the overall thickness of the laminar boundary layer next to container walls but does not eliminate it. Therefore those skilled in the art will recognize that for the purposes of this invention, the reference to the turbulence control will be with respect to the bulk of the fluid, notwithstanding the presence of a minimal amount of laminar flow regime present in the system. See, for instance, McCabe et al, *Unit Operations of Chemical Engineering*, pp. 45–48 (1956).

This invention recognizes that there are two different fluid surfaces in a partially filled reactor vessel—one which is adjacent to the vessel's wall and next to which turbulence is damped by a viscous sublayer, and a free fluid surface where viscosity does not act to damp the turbulent motions. No prior art teaches the necessity of the existence of free turbulent surfaces for the effective control of microorganism growth in closed reactor systems. If a transparent reactor vessel is totally filled with media, a viscous sublayer will retard the motions of the microorganisms in the vicinity of the portion of the wall through which sunlight (or artificial photosynthetic light) penetrates and the "flashing light" control cannot be effectively applied via turbulence control. With a filled apparatus, oxygen removal becomes even more problematical. Furthermore, in a closed reactor vessel in which all surfaces are in contact with the fluid, the viscous layer retards removal of biological particles from the wall which may therefore foul the surface of the reactor. If such fouling occurs on the surface exposed to light, it will act to decrease the penetration of light into the chamber in an exponential relation to the quantity of the fouling, and thereby decrease significantly the potential for photosynthesis. This invention requires the existence of a free liquid medium surface throughout the partially filled growth module, and a moving, turbulent, liquid medium for control of the process, such that the microorganism growth can be optimized and the process thus made commerically viable.

Since a turbulent regime is not established at the same $N_{Re}$ in all systems, or in a single dynamic system and the width of the transition $N_{Re}$ range from laminar to fully turbulent flow is a function of at least two parameters of the system, the liquid flow rate and the wall surface characteristics of the closed flow conduit, control of turbulence in a closed system requires that the operator carefully monitor both of these parameters. Since the surface characteristics, such as smoothness of the conduit walls, change only slowly over time and are not within the control of the operator of the system on a real time basis, the operator utilizes flow rate to control turbulence. As noted above, some transitional turbulence occurs at $N_{Re}<2000$, and full turbulence is present at $N_{Re}$ values in the range of 4000 to $10^6$ depending on the degree of smoothness of the conduit. In the present process the operator will control within this range to obtain turbulence which is correlated with the degree of light intensity to which the microorganisms can be exposed to obtain the optimum yield. This level will change as the culture grows, both because of the change in effective viscosity of the medium due to increase in cell density (which may reduce turbulence) as well as the change of opacity of the medium to light penetration, which requires more frequent visits near the free surface of the fluid in the container. The range of $N_{Re}$=4000 to $10^6$ is the broadest for practical purposes in this process. It is possible to have $N_{Re}>10^6$ (as noted above, common tables go up to $10^8$) but also as mentioned there is little or no significant increase in the level of turbulence above $10^6$, so no significant change in the operation of the present process is obtained. In fact such higher values may be detrimental in that additional pumping power for the greater water flow is needed, greater shearing of the microorganism mass may occur without any countervailing improvement in microbial growth and long chain structures of the microorganism will be broken. On the other hand, $N_{Re}$ must not be too low, since if there is no substantial turbulent regime, the microbial cells well settle out of the medium, the system will become too dense, and there will be little light penetration. Thus it is possible to use the range of $N_{Re}$=2000 to 4000, but since the degree of turbulence there varies substantially, and quite a bit of transitional flow regime may be present, the microbial growth will not be fully directly related to the $N_{Re}$ value and control is usually not adequately precise. Preferred $N_{Re}$ values are in the range of 4000 to 250,000, more preferably 5000 to 50,000. The prior art has not heretofore recognized or described such correlation between the degree of turbulence and the maintenance of the microbial growth rate within the optimum range defined by the principles identified by, e.g., Ryther, supra and Thomas et al, supra.

Dissipation Rate Control:

The requirements of the present invention are based on our discovery of the correlation between amount of turbulence in the aqueous medium and the values of the other parameters related to microbial growth. When $N_{Re}$ is maintained in the ranges we have defined, these other parameters fall within their value ranges which are most conducive to microbial growth, provided the scale of the apparatus is not severely restricted. For instance, microbial growth is a function of the rate at which microorganism cells are able to remove nutrients (nitrogen, phosphorous, etc) from the medium. In the mass culture of microorganisms a key variable one seeks to optimize is nutrient uptake rate. "Nutrient" here is applied broadly to include molecules ranging from inorganic carbon ($CO_2$), nitrogen and phosphorous to organic micronutrients. A stationary cell in a non-turbulent environment will, after some time, remove all the nutrients from its immediate vicinity. This removal will produce a concentration gradient. The uptake rate will then depend entirely upon the concentration gradient in the vicinity of the microorganisms through Fickian diffusion:

$$F=-D\ dC/dz \qquad (1)$$

where F is the nutrient flux, C is the concentration of the nutrient in question and D is the coefficient of molecular diffusion which, for large molecules, is about $1.5\times10^{-9}$ $m^2s^{-1}$; see Munk et al., *J. Marine Res.*, 11:215–240 (1952). Turbulence has a continuum of scales, and on the scale smaller than Kolmogorov scale, defined by $L_K=(v^3/\epsilon)^{1/4}$, viscous diffusive processes deliver nutrients to the cell. The cells are smaller than L, so that their integrity is maintained. Thus, a stationary microorganism cell cannot take up nutrients faster than they are transported to it by diffusion in the smallest eddies. The smaller the scale of dz, the larger the diffusion rate F. For most microorganisms such as phytoplankton, this rate is limiting for growth. In the present process this problem is avoided by increasing the rate of nutrient transport to cells by to increasing the molecular diffusion rate through control of the level of turbulence by increasing $\epsilon$ and thus decreasing L. Thus, the turbulent dissipation rate $\epsilon$ becomes important as the second parameter in our control.

In addition to definition of $N_{Re}$, turbulence control can also be cast as a function of the rate of turbulent energy dissipation $\epsilon$ which allows a scale definition. Turbulence is manifest in water across even the smallest distances by a linear shear whose magnitude depends on the strength of the turbulence. Shear is a property of the fluid and exists whether microorganisms are present or not.

The effect of an increase in diffusive flux due to turbulence has been discussed in Mann et al., *Marine Ecosystem Dynamics* (1991), who show that increase in nutrient flux is dependent on both the turbulent energy dissipation rate, $\epsilon$, and on the size of the microorganism cell. For example, a cell of approximately 50 μm diameter can experience a 100% increase in nutrient flux at a turbulent energy dissipation rate $\epsilon=10^{-3}$ W/kg. In the present process, using a system of the type to be described below, turbulent energy dissipation rates between and $10^{-3}$ and 10 W/kg can be produced.

The turbulent energy dissipation rate is given by:

$$\epsilon=v(\partial u/\partial z)^2 \quad (2)$$

where $\epsilon$ is the turbulent energy dissipation rate, v is the kinematic viscosity ($10^{-6}$ m$^2$s$^{-1}$) and $\partial u/\partial z$ is the velocity gradient in the turbulence field. In turbulent flow the parameter z scales as $\alpha L_k N_{Re}^{-1/2}$, from which it follows that $$\epsilon=(vu^2 N_{Re})/\alpha^2 L_k^2 \quad (3)$$

where u is the velocity of flow in the conduit, $L_k$ is the diameter of the conduit and $\alpha$ is an order one constant, or directly by substituting for ($N_{Re}$)

$$\epsilon=u^3/\alpha^2 L_k \quad (4)$$

The dependence of $\epsilon$ on both Reynolds Number and conduit diameter is given by $$\epsilon=(v^3 N_{Re}^3)/\alpha^2 L_k \quad (5)$$

Thus, it is evident that not only must one choose $N_{Re}$ for optimum level of turbulent exposure to light, but also a scale, $L_k$, for turbulent delivery of nutrients to the cells.

Exemplary Apparatus Configuration:

The basic principles and processes involved in the application of these control parameters and the assumed mechanisms described above will be better understood when discussed in the context of an exemplary microorganism growth system. Such a typical system is illustrated schematically in the FIGURE. The system may be partitioned into three principal functions: water pretreatment, microbe production, and harvesting. Such a system may be capable of maximum conservation of water resources by recycling all water not subject to evaporation. It will be understood that the control parameters of this invention are applied in the bioreactor growth module 14, i.e., the microbe production component. (There may be a plurality of growth modules 14 operating in parallel, but for brevity herein the description will be given in terms of a single growth module 14.)

In the water pretreatment stage, water is pumped from a water source 2 (fresh or marine), preferably passed through a filter 4, and then may be pumped into a large holding reservoir 6. Preferably the cover of the holding reservoir 6 will be made from a dark plastic material, e.g., black polyethylene, to prevent contamination of the prefiltered water and promote heating without exposing the prefiltered water to sunlight, which can encourage unwanted premature growth of photosynthetic microorganisms in the holding reservoir. Filtration may be accomplished by a variety of conventional techniques, such as rapid sandbed filtration for large quantities of water or diatomaceous earth for smaller quantities. Under certain circumstances, filtration may not be necessary, such as in the use of deep ocean water from oligotrophic regions or in the use of particulate-free water from certain aquifers. If the water is already free of particulates, filtration can be eliminated.

Preheating of the water is preferably accomplished by passive solar heating 8 in a covered holding reservoir (which may be the same as reservoir 6). The preheating process may be necessary in the case of relatively cool source water, such as non-geothermal ground water which may be at a lower temperature than is required for optimal growth of many species of microbes (between about 24°–35° C. [75°–95° F.]). Thus, preheating permits the temperature of the culture to be adjusted appropriately prior to introduction into the circulating growth system. When the water from the source is already at an appropriate culture temperature, the preheating step can be eliminated. Further, while solar heat is preferred for economic and environmental reasons, other sources of heat such as a conventional heater could be used to provide the necessary temperature adjustment.

A sterilization step 10 may be necessary in the case of source water expected to contain living microorganisms or potential predators, which might threaten the viability of the desired microorganisms being grown in the culture system. The preferred method of sterilization is by treatment of the medium with ultraviolet light, gamma radiation, ozone, or any other non-invasive sterilization agent, or it may also be accomplished by other conventional means. In many cases, the prior filtration step can be expected to eliminate living particles. If analysis of the source water or effectiveness of the filtration indicates no substantial contamination of the water with unwanted microorganisms or potential predators, the sterilization step is not required.

The microorganism feedstock is provided to an appropriate reaction vessel or "bioreactor," here defined as a growth module 14, from a makeup vessel 42. Makeup water (which may be conditioned with nutrients and other desired additives) and a microorganism inoculum are introduced into vessel 42. As an example, one might use 30 liters of culture for the inoculation, in which case the initial volume of makeup water added would be approximately 150 liters. Although the ratios of concentrated laboratory inoculum to fresh makeup water will be species dependent, and optimum ratios will be determined empirically, the ratio will generally be in the range of 5:1 to 10:1. After a short stabilization period in vessel 42, the water/inoculum mixture is transferred to one of the growth modules 14. There is an initial period of growth of inoculum in the module 14, which will generally last for only a few days. Thereafter as the microorganism grows and the biomass increases, there is continued addition of fresh makeup water and nutrients, either manually or automatically, while the turbulent regime is maintained. Continued expansion of the system to full operating capacity is a simple matter of replication.

Nutrients are normally be added to the water as it enters the growth module 14 as indicated at 12. In the production state, water is distributed from the holding reservoir 6 through the sterilization processor 10 to individual growth modules 14. If the holding reservoir is maintained at a higher elevation than the growth modules, distribution from the holding reservoir can be accomplished under the force of gravity. Otherwise, a pump is required to feed the water into the growth module 14.

The growth module 14 will be greater in volume than the volume of the aqueous medium, i.e., the growth module is not completely filled with the aqueous medium. This is necessary so that effective turbulence can be achieved. If the module is full, there is a wall effect which causes cells to accumulate at the wall and become trapped there, causing light saturation of those cells and, by blocking light, causing light starvation of the cells in the interior of the aqueous medium. If the module is kept only partially filled, there is a free medium surface present which permits effective turbulent motion of the bulk medium and prevent the accumulation of stagnant cell masses at the conduit surface. Further, substantial oxygen gas is evolved during cell growth. If the growth module is full of the aqueous medium, removal of the evolved oxygen gas is hindered and the system can suffer oxygen poisoning. Finally, keeping the module less than full of the aqueous medium means that the system can operate at essentially ambient pressure instead of overpressure, and that ordinary transparent flexible tubing can be used as the conduit in the growth module, rather than requiring expensive pressure resistance rigid tubing. The filled volume can be any convenient amount, and will generally be in the range of about 30%–90%. If the volume is too close to completely full, the wall effect and gas removal problems will predominate, while if the volume is too low, the system will not be utilized efficiently. Those skilled in the art will be readily able to determine an appropriate fill volume for any particular apparatus.

Typically the growth modules 14 are tubular and made of polyethylene, although any rigid or flexible material not harmful to plant tissue can be used providing it is substantially insoluble and impermeable to water, transparent to visible light, but impervious to near-visible ultraviolet light. While low density polyethylene is most preferred for this purpose (particularly if it is of minimum thickness so as to reduce both light attenuation and cost), other possible materials include polypropylene, polyacrylate, polyamide, polycarbonate, water insoluble cellulose ester and polyester films, or (less preferred) glass.

The growth module will be of a size to provide the required ratio of the scale of the apparatus to the scale of the turbulent eddies maintained during the growth process. We have found that the level of fluid in the flowing-fluid reaction chamber relative to eddy scale, $\lambda_K$, should be in the range of 10–1:1, and preferably in the range of 10–1.2:1. If the ratio is too great (i.e., >10:1) then cells are damaged, $\epsilon$ is too high, and $N_{Re}$ limits growth. Conversely, if the ratio is too low (i.e. <1:1) then the scale of the eddies will exceed the size of the vessel and the eddies will not be properly maintained in their three dimensional stirring process. This latter would occur if a very deep and narrow conduit is used. It will be recognized that there will be a large number of eddies present at most times during the operation of the process, with a wide variety of eddy sizes represented. For the purpose of this invention, we will refer to a "predominant eddy volume," which can be defined generally as what would be a theoretical eddy size if all of the actual eddies were considered to be uniform in size with each other. In other words, what would be the "average" eddy size if the total eddy volume were distributed evenly over the same total number of eddies. Those skilled in the art will have no difficulty in applying this value on an empirical basis, since it is essentially what one would calculate as a statistical "average" eddy from the observed turbulence properties of the actual bulk volume of the aqueous medium during operation.

The growth module 14 will commonly be provided with a means for collecting dissolved gases 16, such as oxygen, which are produced during photosynthesis by the microorganisms being grown therein. The growth module, which is described in greater detail hereinafter, may be characterized as a closed, controlled, continuous growth environment for photosynthetic microbes.

Harvesting is normally accomplished by a separation process, preferably a multi-stage process, with concentration of microbial biomass increasing at each step until a final wet or dry product is obtained. There are, however, some applications where further treatment of the grown microbial mass is not required and the harvested culture in suspension is used directly as a product. For instance, where microbes are not required to be harvested as a dewatered "wet" product 34 or a dried product 38, such as in some cases where they will be used as a feed slurry for a chemical extraction process, the harvesting steps may be eliminated. In such cases, output harvest from the growth modules 14 may be pumped or passively moved by gravity into such secondary processing systems 18, either directly or indirectly after being held in intermediate storage vessels (not shown).

The first step of harvesting may be flocculation 20. Harvest water is pumped, or allowed to flow by gravity, from the growth module 14, flushing out the photosynthetic microorganisms grown therein. After leaving the growth module 14, the harvest water may pass through an electroflocculator which creates large aggregates of microbes. Alternatively, flocculation 20 may be accomplished by the addition of chemical flocculants, such as alum, to the medium as it enter the sedimentation tanks 22. The aggregates produced by flocculation should, preferably, have sedimentation rates at least two orders of magnitude greater than those of the individual microbial cells of which they are composed. Some species of microalgae or plant tissues may autoflocculate (e.g., Haematococcus species), in which case no flocculation step is required.

Immediately after leaving the flocculator 20, the harvest water, containing the large aggregates of microorganisms, is passed into a series of sedimentation tanks 22. Sedimentation generally takes place in several hours, concentrating the microorganisms by a factor of about fifty and yielding a concentrated floc 24 and a supernatant liquid 26.

The next step of the harvesting procedure is centrifugation 28. Concentrated microbial floc 24 may be removed from the sedimentation tanks 22 and passed into a high volume, continuous centrifuge in which is it centrifuged (normally at 3,000 to 30,000 rpm) to produce a supernatant 26' and a concentrated microbial slurry 30 having 70% to 90% water. The high speed continuous centrifugation 28 provides yet a further dewatering step, concentrating the microbial biomass by a factor of 20–50, to produce the desired "wet" product 34.

The combined supernatants 26 and 26' from the sedimentation tanks 22 and the centrifuge 28 may be disposed of in any convenient manner as indicated at 40, but preferably will be passed to a percolation field 32 from which it may be recycled into the water source (e.g., an aquifer) 2. Percolation underground or otherwise in the absence of light serves to kill any photosynthetic microbes which remain in the supernatant, so that they are not introduced into the water source 2. Natural percolation processes also serve to strip the medium of most dissolved organic and inorganic materials, thus providing generally pure recycled water to the source 2.

An optional additional harvesting step employs a drying surface 36. Microbial concentrate from the centrifuge 28 is distributed in a thin layer atop a surface of concrete, plastic, glass, or any other uniformly smooth and planar surface. Drying of the slurry concentrate 30 to produce a "dry" product 38 is normally accomplished by evaporation, although supplemental drying such as with hot air may also be used. Maximum evaporation rates are preferably maintained by covering the drying surface and automatically controlling the relative humidity and temperature within the covered housing.

Control Method Advantages:

Using systems such as this exemplary system, the control method of the present invention provides advantages not possible from any prior art control method. First, the method will achieve a turbulent energy dissipation rate $\epsilon$ of a value which enhances nutrient uptake at reasonable flow rates. Second, $\epsilon$ can be much more closely controlled, especially when larger diameter conduits are used. For instance, reference to equation (5) shows that for a pipe diameter of 25 cm (10 in), $\epsilon$ will fall in the range of enhancing nutrient uptake rate ($>10^{-3}$ W/kg) at $N_{Re}>15,000$. At such conduit diameter, these Reynolds Numbers are achieved at fluid velocities greater than about 5 cm/sec. Thus, $\epsilon$ of a value required for enhancing nutrient uptake can be produced at by the turbulence created at reasonable flow rates.

Secondly, it will be seen from equations (4) and (6) that fairly small variations in flow rate will cause great fluctuations in $\epsilon$ (since $\epsilon \propto u^3/L_k$). For equivalent values of $\epsilon$, fluctuations in velocity can therefore be more precisely controlled with larger conduit diameters. With smaller diameters, a given increase in $\epsilon$ is produced by small increases in fluid flow rate. However, for the same increase in $\epsilon$ to occur in a larger diameter conduit would require a much greater increase in flow velocity, permitting more precise control by providing for many more incremental changes in flow velocity. Further, since $$\epsilon = kQ^3/L_k^7 \qquad (6)$$

where k is a constant, Q is the area flow rate (production rate) and $L_K$ is the conduit diameter, for a given value of $\epsilon$ the microorganism production rate goes up as slightly more than the square of the conduit diameter. Thus, in systems with larger conduit diameters each maintaining the same value of $\epsilon$ (to promote optimization of nutrients), the actual production rate will be significantly greater than in systems with substantially smaller conduit diameters.

Control by use of turbulence in the fluid flow accomplishes a number of desirable results. Turbulence will keep cells of certain photosynthetic microorganisms from settling out of the circulating water. This occurs particularly if they are not flagellated (e.g., diatoms, or Bacillariophycae) and thus cannot provide their own locomotion. Turbulent flow also insures that all the cells in the growth medium are exposed to light which, in a dense culture, would otherwise be expected to be almost entirely extinguished at a depth equal to approximately 10% of the depth of the culture. The circulating/growth mode of turbulence is allowed to continue for a time sufficient to monitor and determine the optimal level(s) of turbulence and once determined, to allow the photosynthetic microorganisms to grow to a predetermined optimal biomass before harvesting. The use of turbulence control enhances population growth by using the aforementioned "flashing light effect" to advantage. The flashing light effect is, in essence, a function of the ability of photosynthetic cells to only absorb a finite quantity of radiated energy from light. As a result, many of such cells may benefit as much from intermittent exposure to a light source as they would from continuous exposure. In fact, given that certain cells are damaged by continuous exposure to light, intermittent exposure of cells to light in a turbulent flow regime can reduce cell loss. By adjusting the turbulence to which cells are exposed an operator of a growth system can maximize cell productivity from the flashing light effect while minimizing cell loss from overexposure to light and shear.

The turbulence can be controlled in a variety of manners, using either or both equipment parameters or fluid parameters. For instance, from the definition of $N_{Re}$, it will be seen that turbulence control may be by modifying flow velocity or the diameter of the growth tubes. Once the desirable level of turbulence is determined, velocity and/or the diameter of the growth tubes used can be adjusted accordingly. Therefore, for purposes of describing this invention no specific values for tube diameter, flow velocity or fluid viscosity will be provided because it is assumed that the operator of the invention will determine for the cells to be cultured which value of $N_{Re}$ is desired according to the means for making that determination taught herein and will be able to adjust the components of tube diameter and/or flow velocity accordingly.

It will be recognized that the control parameters applied to growth module 14 will vary over the course of each growth cycle, since as microbial growth develops the various requirements of light availability to increasing numbers of cells, nutrient requirements and delivery, total gas generation, etc. will vary. Thus the method of the present invention will be recognized to be a continuous control method, where the turbulence control level at any time is a function of the progress of the microbial growth cycle.

During operation of the system, the physical, chemical and biological characteristics of the growth medium are continuously monitored, usually at several monitor stations across the system. Properties commonly monitored include pH, $CO_2$ content, temperature, optical density (biomass) and flow velocity. Acceptable values of each will vary over ranges dependent upon the particular microorganism(s) being grown, and those skilled in the art will be able readily to determine the optimum values for these properties for the microorganism(s) of interest. These will change also with the residence time of the microorganisms in the growth module. As guidance, we have found that when, e.g., *Haematococcus pluvialis, Spirulina platensis, Lyngbya lagerheimii,* or *Chlorella sorokiniensis* are grown in a system of the type illustrated in the FIGURE with 24 cm diameter closed conduits, suitable ranges of parameters are:

| | |
|---|---|
| $N_{Re}$ | 4000 to $10^6$ |
| pH | 6.5 to 9.5 |
| $CO_2$ content | 100 g/m$^3$ to solubility limit |
| temperature | 25°–35° C. (75°–95° F.) |
| $\lambda_K$ | 1–10 |
| flow velocity | 2–100 cm/sec |

While optimum pH level will vary with the species of photosynthetic microorganism being cultured, pH levels will normally be in the range of 6.5–9.5 for optimum growth. The turbulence control will normally produce the desired pH values. If desired, pH values may be further regulated by chemical addition; high pH may be reduced by adding either $CO_2$ or acid (preferably $HNO_3$), while low pH can be raised by adding base (preferably $NH_4OH$). Further, by selecting nitrogenous acids and bases, pH regulation simultaneously adds nutrients to the medium. Depending on the nutritional requirements of the species being cultured, phosphorylated acids and bases may be used if phosphorous is preferred over nitrogen as the primary limiting nutrient. This is controlled by selecting a $\lambda_K$ which is based on the length of the air-lift or gas exchange system.

The optimal rage of gas content ($CO_2$) will also be species dependent, but in all cases will be greater than 100 g/m³ of carbon as either $CO_2$, carbonate or bicarbonate, and in no case will exceed the solubility of $CO_2$ in water. If the $CO_2$ concentration provided by the turbulence control is observed to be below the optimum range, gaseous $CO_2$ from a supply tank can be added to the system. As noted above, $CO_2$ addition may also be used to regulate pH. This is the preferred method of increasing acidity if $CO_2$ levels are low and nutrient concentrations are high, whereas the addition of acid is preferred when $CO_2$ levels are high and nutrient levels are low.

The biomass of photosynthetic microorganisms in the culture is determined by optical methods. In one method, measurements are made by reading optical density, but alternate optical methods may be appropriate, such as in vivo fluorescence of chlorophyll or other fluorescent pigments. Since optical density and pigment concentrations are proportional to the biomass of microbes, these methods provide a measure of the concentration of microbes present at each monitoring location within the culture. Thus, the difference in cell concentration between two monitoring locations, separated by a known distance, which requires a known time to be traversed, can be used to calculate the amount of cell material produced in that period of time. Thus, productivity can be readily determined and improved or optimized by any user of this system.

Temperature control is also very important. All photosynthetic microorganisms grow optimally within rather narrow temperature ranges, with growth often decreasing significantly when temperature falls 2°–3° C. (3°–4° F.) outside the optimal range. The fastest-growing species usually grow optimally in the range of 25°–35° C. (75°–95° F.); Eppley, *Fishery Bull. U.S.*, 70:1063–1085 (1972). In general, growth rate increases slowly with increasing temperature, and then declines more rapidly at temperatures above optimum. Turbulence assures that temperature is well mixed in the fluid medium and that no cold spots occur.

Nutrients which are provided to the system at 12 will include any nutrients as necessary for the optimal growth of a particular microbial species being cultured. These may include, for example, superphosphate, urea, silicate, trace metals such as zinc, iron, vanadium, etc., vitamins, and other growth enhancing materials. The nutrients are normally provided in a form in which they are concentrated relative to the final concentration in the growth system; a typical concentration factor is approximately 4000. Typically the nutrients are added to the fresh culture water at a rate of approximately 0.5 ml/sec for each three hour harvest/refill period. The rate of nutrient addition is adjusted to rapidly bring nutrient concentrations within the culture medium to predetermined optimal levels. These levels are selected on the basis that all nutrients will be consumed by the end of the growth cycle. Alternatively, the addition of nutrients can be controlled (such as by microprocessors based upon readings by sensors placed at appropriate points in the system) in an analogous manner to the pH and $CO_2$ control previously described. Systems will commonly store sufficient nutrient supplies for operating the growth modules 14 for several months.

The turbulence control method of the present invention is applicable to growth of a wide variety of microorganisms. These will include numerous genera of algae, unicellular phytoplankton, tissues of vascular plants, tissues of microalgae and the like. Typical examples of specific genera and species whose growth on a commercially viable basis can be controlled by turbulence control include Dinophyceae, Bacillariophyceae, *Lyngbya lagerheimii* (Cyanophyceae), *Spirulina platensis* (Cyanophyceae), *Haematococcus pluvialis* (Chlorophyceae), *Chlorella sorokiniensis* (Chlorophyceae), and plant cell tissue cultures. Particularly preferred for growth by means of the claimed invention are *Haematococcus pluvialis, Spirulina platensis, Lyngbya lagerheimii,* and *Chlorella sorokiniensis.* Those skilled in the art will immediately recognized that this list is not exclusive and that many other genera and species will also be amenable to growth processes utilizing the turbulence control techniques of the present invention.

Many of these microorganisms are particularly valuable for commercial growth, since they produce naturally either directly or indirectly chemicals which otherwise would have had to have been made synthetically, from petrochemical, coal-based or similar feedstocks. Typical of such chemicals which can be obtained from such microorganisms are colorants such as chlorophylis, xanthophylls, and carotenoids; fatty acids such as gamma-linoleic acid, carbohydrates such as glucose, alcohols such as glycerol, petroleum hydrocarbons, and all manner of naturally-occurring chemical compounds as have been, or might be expected to be found, in the approximately 30,000 species of microalgae known to exist in nature. Also included as potential organisms are tissues of common vascular plants typically used as a source of valuable commodities such as coffee, tobacco, chocolate, rubber, etc. Those skilled in the art will of course be aware of numerous other end products derived from microorganisms which could advantageously be produced using systems incorporating the turbulence control method of the present invention.

It will be evident that there are numerous embodiments of this invention which, while not expressly described above, are clearly within the scope and spirit of the invention. The above description is therefore to be considered exemplary only, and the actual scope of the invention is to be determined solely from the appended claims.

We claim:

1. A method for the control of an aqueous microorganism growth process which comprises:

distributing a photosynthetic microbial biomass in an aqueous medium within a reaction chamber, said reaction chamber being transparent to visible light, and said aqueous medium containing a suspension of microbial biomass occupying less than the total volume of said chamber;

maintaining said biomass within said reaction chamber for a period of time during which microorganisms comprising said biomass reproduce and increase in number;

providing nutrients to and removing evolved gases from said biomass during said period of time to support said reproduction;

flowing quantities of said aqueous medium through said reaction chamber throughout said time period;

subjecting said reaction chamber to a source of visible light for at least a portion of said period of time with said visible light passing into said reaction chamber and being used by said microorganisms to enable photosynthesis;

maintaining a turbulent flow regime with turbulent eddies predominantly throughout said aqueous medium within said reaction chamber for said period of time;

maintaining a predetermined range of ratios between scale of said chamber and scale of said eddies for said period of time;

such that in said turbulent flow regime effective reaction conditions are maintained for said reproduction of said microorganisms until said time period has been sufficient to produce a desired increase in number of said microorganisms.

2. A method as in claim 1 wherein said turbulent flow regime is defined by a Reynolds Number value of between 2000 and $10^6$.

3. A method as in claim 2 wherein said turbulent flow regime is defined by a Reynolds Number value of between 4000 and $10^6$.

4. A method as in claim 3 wherein said turbulent flow regime is defined by a Reynolds Number value of between 4000 and 250,000.

5. A method as in claim 4 wherein said turbulent flow regime is defined by a Reynolds Number value of between 5000 and 50,000.

6. A method as in claim 1 wherein said range of ratios is 10–1:1.

7. A method as in claim 6 wherein said range is 10–1.2:1.

8. A method as in claim 1 wherein said microbial biomass comprises at least one type of microorganism from the group selected from unicellular phytoplankton, tissues of vascular plants and tissues of macroalgae.

9. A method as in claim 8 wherein said microorganism or tissues of the aforementioned plants is selected from the group consisting of Dinophyceae, Bacillariophyceae, *Lyngbya lagerheimii* (Cyanophyceae), *Spirulina platensis* (Cyanophyceae), *Haematococcus pluvialis* (Chlorophyceae), *Chlorella sorokiniensis* (Chlorophyceae), and plant cell tissue cultures.

10. A method as in claim 9 wherein said microorganism is selected from the group consisting of *Haematococcus pluvialis, Spirulina platensis, Lyngbya lagerheimii,* and *Chlorella sorokiniensis.*

11. A method as in claim 1 wherein said reaction conditions in said reaction chamber comprise light exposure, nutrient supply, sedimentation rate, bulk temperature, gas exchange rate and cell integrity.

12. A method as in claim 1 wherein said turbulent flow regime causes movement of said microorganisms within said biomass such that exposure of individual microorganisms to said visible light is intermittent.

13. A method as in claim 12 wherein said intermittent exposure of visible light to said microorganisms creates a flashing light effect on the photosynthesis produced in said microorganisms.

14. A method as in claim 13 wherein said microorganisms are exposed to said visible light for a cumulative time of approximately ten times longer than the cumulative time of non-exposure.

15. A method as in claim 1 further comprising maintaining a turbulent energy dissipation rate $\epsilon$ between $10^{-3}$ and 10 W/kg.

16. A method as in claim 1 wherein said aqueous medium containing said microbial mass occupies approximately 30%–90% of the total volume of said chamber.

* * * * *

UNITED STATES PATENT AND TRADEMARK OFFICE
CERTIFICATE OF CORRECTION

PATENT NO. : 5,541,056
DATED : July 30, 1996
INVENTOR(S) : Mark E. Huntley, Pearn P. Niiler and Donald Redalje It is certified that error appears in the above-indentified patent and that said Letters Patent is hereby corrected as shown below:

- COVER PAGE, UNDER "RELATED U.S. APPLICATION DATA [63]," AFTER "OCT. 10," DELETE "1982" AND INSERT --1989--.

Signed and Sealed this

Twelfth Day of November, 1996

Attest:

BRUCE LEHMAN

Attesting Officer      Commissioner of Patents and Trademarks